(12) United States Patent
Kuroiwa et al.

(10) Patent No.: US 10,213,185 B2
(45) Date of Patent: Feb. 26, 2019

(54) ULTRASONIC DIAGNOSTIC APPARATUS

(71) Applicant: Toshiba Medical Systems Corporation, Otawara-shi (JP)

(72) Inventors: Koji Kuroiwa, Nasushiobara (JP); Kazuhito Nakata, Otawara (JP); Gen Nagano, Nasushiobara (JP); Kenichi Unayama, Otawara (JP); Takeshi Fukasawa, Nasushiobara (JP); Fumio Mochizuki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 713 days.

(21) Appl. No.: 14/858,946

(22) Filed: Sep. 18, 2015

(65) Prior Publication Data

US 2016/0007955 A1 Jan. 14, 2016

Related U.S. Application Data

(63) Continuation of application No. PCT/JP2014/057126, filed on Mar. 17, 2014.

(30) Foreign Application Priority Data

Mar. 18, 2013 (JP) .................................. 2013-055510

(51) Int. Cl.
*A61B 8/00* (2006.01)
*A61B 8/08* (2006.01)
(Continued)

(52) U.S. Cl.
CPC .............. *A61B 8/4254* (2013.01); *A61B 8/06* (2013.01); *A61B 8/4444* (2013.01); *A61B 8/463* (2013.01);
(Continued)

(58) Field of Classification Search
CPC ... A61B 2090/3925; A61B 8/06; A61B 8/085; A61B 8/4254; A61B 8/4444; A61B 8/463; A61B 8/469; A61B 8/488; A61B 8/54

See application file for complete search history.

(56) References Cited

U.S. PATENT DOCUMENTS 5,476,097 A 12/1995 Robinson
2005/0119569 A1 6/2005 Ohtake

FOREIGN PATENT DOCUMENTS

JP 08-229035 A 9/1996
JP 11-299785 A 11/1999
(Continued)

OTHER PUBLICATIONS

International Search Report dated Apr. 28, 2014 for PCT/JP2014/057126 filed Mar. 17, 2014 with English Translation.
(Continued)

*Primary Examiner* — Michael T Rozanski
(74) *Attorney, Agent, or Firm* — Oblon, McClelland, Maier & Neustadt, L.L.P.

(57) ABSTRACT

A converting circuitry convert position information on at least one of an ultrasonic probe and a scan area, used in a past ultrasonic scan, into first position information based on a predetermined coordinate system. The converting circuitry further convert position information on at least one of ultrasonic probe and a scan position, used in a current ultrasonic scan, into second position information based on the predetermined coordinate system. The display circuitry determine the position of a first marker, which represents at least one of the ultrasonic probe and scanning area used in a past ultrasonic scan, and a second marker, which represents at least one of the ultrasonic probe and scanning area used in a current ultrasonic scan, based on first position (Continued)

information and second position information, and display the first and second markers.

10 Claims, 9 Drawing Sheets

(51) Int. Cl.
*A61B 8/06* (2006.01)
*G06F 19/00* (2018.01)

(52) U.S. Cl.
CPC .............. *A61B 8/488* (2013.01); *G06F 19/00* (2013.01); *A61B 8/085* (2013.01); *A61B 8/469* (2013.01); *A61B 8/54* (2013.01)

(56) References Cited

FOREIGN PATENT DOCUMENTS

| | | |
|---|---|---|
| JP | 2000-107185 A | 4/2000 |
| JP | 2004-194705 A | 7/2004 |
| JP | 2005-124712 A | 5/2005 |
| JP | 2006-271862 A | 10/2006 |
| JP | 2009-089736 A | 4/2009 |
| JP | 2011-110182 A | 6/2011 |
| WO | WO 2006-059668 A1 | 6/2006 |
| WO | WO 2012/080957 A2 | 6/2012 |

OTHER PUBLICATIONS

International Written Opinion dated Apr. 28, 2014 for PCT/JP2014/057126 filed Mar. 17, 2014.
Office Action dated Apr. 18, 2017 in Japanese Patent Application No. 2013-055510.

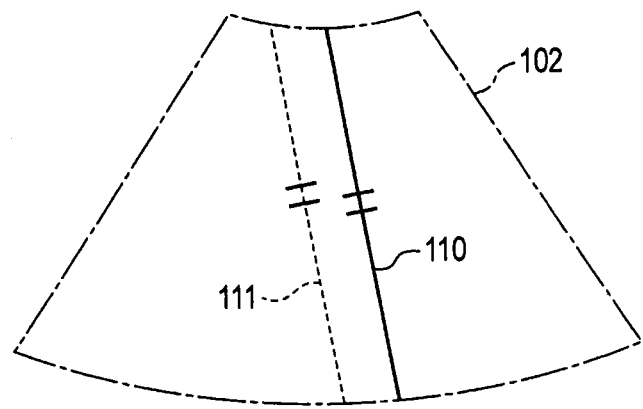
F I G. 10

ULTRASONIC DIAGNOSTIC APPARATUS

CROSS-REFERENCE TO RELATED APPLICATIONS

This application is a Continuation application of PCT Application No. PCT/JP2014/057126, filed Mar. 17, 2014 and based upon and claims the benefit of priority from the Japanese Patent Application No. 2013-055510, filed Mar. 18, 2013 the entire contents of all of which are incorporated herein by reference.

FIELD

An embodiment of the present invention relates to an ultrasonic diagnostic apparatus.

BACKGROUND

An ultrasonic diagnostic apparatus that visualizes body tissues of a patient in a non-invasive manner has a function of measuring the rate of blood flowing through a blood vessel of a patient (flow velocity). Typically, the flow velocity measured based on this function is used for generating a color Doppler image representing the flow velocity distribution in a blood vessel and for generating a Doppler spectrum image representing the time change in flow velocity vary with time. These images are referred to, for example when the flow velocity is checked for a follow-up and when the flow velocity is monitored before and after a surgical operation.

In the measurement of the flow velocity, the flow velocity is calculated based on changes in the frequency of an ultrasonic wave transmitted and received and the angle between the direction in which an ultrasonic wave is transmitted and received and the direction in which the blood flows. The frequency of an ultrasonic wave reflected by the blood flow and then received undergoes a Doppler shift in accordance with the motion of the blood flow. As a result, the frequency is shifted to a frequency higher or lower than the frequency of a transmitted ultrasonic wave. The frequency shift amount is dependent on the motion speed of the blood flow. On the other hand, the angle between the direction in which an ultrasonic wave is transmitted and received and the direction in which the blood flows is dependent on the position and angle of an ultrasonic probe pressed against the patient and on the angle at which an ultrasonic beam is transmitted and received by the ultrasonic probe. Therefore, the calculated flow velocity is greatly dependent upon the angle between the direction in an ultrasonic beam and the direction in the blood flows.

BRIEF DESCRIPTION OF THE DRAWING

FIG. 10 is a schematic diagram illustrating a B-mode image according to the embodiment.

DETAILED DESCRIPTION

In general, according to one embodiment, an ultrasonic diagnostic apparatus comprising a converting circuitry and a display control circuitry. The converting circuitry convert position information on at least one of an ultrasonic probe and a scan position, used in a past ultrasonic scan of an examinee, into first position information based on a predetermined coordinate system, and which further converts position information on at least one of ultrasonic probe and a scan position, used in a current ultrasonic scan of the examinee, into second position information based on the predetermined coordinate system. The display control circuitry determine a position of a first marker, representing at least one of the ultrasonic probe and scan position used in the past ultrasonic scan, and a position of a second marker, representing at least one of the ultrasonic probe and scan position used in the current ultrasonic scan, based on the first position information and the second position information, and display the first and second markers.

Embodiments will now be described with reference to the accompanying drawings.

Figure 1:
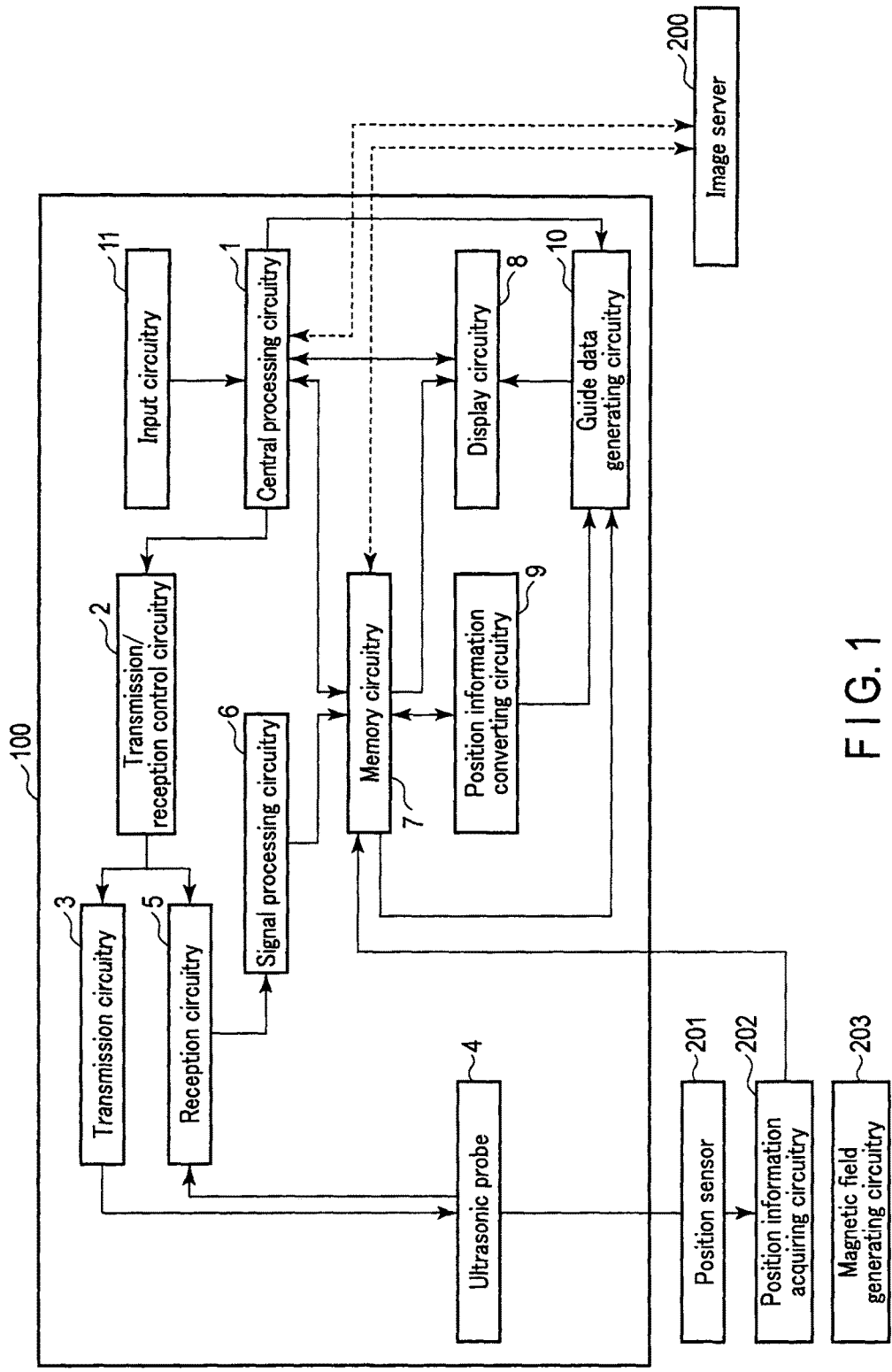
FIG. 1 is a block diagram illustrating an ultrasonic diagnostic apparatus of a first embodiment.

First, the configuration of an ultrasonic diagnostic apparatus 100 according to the present embodiment will be described with reference to the block diagram shown in FIG. 1.

The ultrasonic diagnostic apparatus 100 of the present embodiment comprises a central processing circuitry 1, a transmission/reception control circuitry 2, a transmission circuitry 3, an ultrasonic probe 4, a reception circuitry 5, a signal processing circuitry 6, a memory circuitry 7, a display circuitry 8, a position information converting circuitry 9, a guide data generating circuitry 10 and an input circuitry 11. The ultrasonic diagnostic apparatus 100 is connected to an image server 200 for the transmission and reception of data by way of a network.

A description will be given of an outline of the present embodiment. The position information converting circuitry 9 converts position information on at least one of an ultrasonic probe and a scanning area used in a past ultrasonic scan of an examinee into first position information based on a predetermined coordinate system. In addition, the position information converting circuitry 9 converts position information on at least one of an ultrasonic probe and a scanning area used in a current ultrasonic scan of the same examinee into second position information based on the predetermined coordinate system. The ultrasonic scan according to the present embodiment is applicable to any scan mode, including the B-mode, color Doppler mode and Doppler spectrum mode. In the case of the B mode, the scanning area is set as either a two-dimensional space (scanning plane) or a three-dimensional region (scanning volume). In the case of the color Doppler mode, the scanning area is set as either a scanning plane or a region of interest (ROI) included in the scanning volume. In the case of the Doppler spectrum mode, the scanning area is set as either a scanning plane or a single scanning line included in the scanning volume. The display circuitry 8 determines the position of a first marker (which represents at least one of the ultrasonic probe and scanning area used in a past ultrasonic scan) and a second marker (which represents at least one of the ultrasonic probe and scanning area used in a current ultrasonic scan) based on first position information and second position information, and displays the first and second markers.

A detailed description will be given of the configuration of the present embodiment.

In the descriptions below, control data is intended to refer to data required for an ultrasonic probe 4 to generate an ultrasonic transmission beam. To be more specific, the control data include delay time information for delaying a driving pulse to be supplied to the transducer of the ultrasonic probe 4.

Upon reception of an instruction to generate B-mode data from the input circuitry 11, the central processing circuitry 1 generates control data used for generating B-mode data, and transfers the B-mode-data-generation control data to the transmission/reception control circuitry 2. Upon reception of an instruction to generate color Doppler data from the input circuitry 11, the central processing circuitry 1 generates control data used for generating color Doppler data in the range designated from the input circuitry 11, and transfers the color-Doppler-data-generation control data to the transmission/reception control circuitry 2. Upon reception of an instruction to generate Doppler spectrum data from the input circuitry 11, the central processing circuitry 1 generates control data used for generating Doppler spectrum data at the position designated from the input circuitry 11, and transfers the Doppler-spectrum-data-generation control data to the transmission/reception control circuitry 2. In connection with the present embodiment, reference will be made to the case where Doppler spectrum data is generated by executing sampling in the pulse Doppler method.

In accordance with instructions from the input circuitry 11, the central processing circuitry 1 transfers the B-mode data, color Doppler data and Doppler spectrum data used in a past scan from the memory circuitry 7 to the display circuitry 8. In accordance with instructions from the input circuitry 11, the central processing circuitry 1 transfers the B-mode data, color Doppler data and Doppler spectrum data currently acquired by a live scan from the memory circuitry 7 to the display circuitry 8.

In accordance with instructions from the input circuitry 11, the central processing circuitry 1 transfers three-dimensional medical-image data (volume data), such as data on an X-ray CT image, an MRI image and an ultrasonic image, from the image server 200 to the memory circuitry 7, and stores the medical-image data in the memory circuitry 7. The central processing circuitry 1 functions as a display controller as well. For example, in accordance with an instruction from the input circuitry 11, the central processing circuitry 1 transfers the volume data from the memory circuitry 7 to the display circuitry 8. In accordance with an instruction from the input circuitry 11, the central processing circuitry 1 transfers the volume data from the memory circuitry 7 to the position information converting circuitry 9.

The central processing circuitry 1 controls the memory circuitry 7 to store position information acquired by a position information acquiring circuitry 202 and representing the position of the ultrasonic probe 4 in a past scan. The central processing circuitry 1 controls the memory circuitry 7 to store position information acquired by the position information acquiring circuitry 202 and representing where the ultrasonic probe 4 is currently located in a real space. The central processing circuitry 1 transfers the position information on the ultrasonic probe 4 from the memory circuitry 7 to the position information converting circuitry 9. The central processing circuitry 1 transfers the position information on the ultrasonic probe 4 from the memory circuitry 7 to the guide data generating circuitry 10. Details of the position information on the ultrasonic probe 4 will be described later.

The central processing circuitry 1, functioning as a display controller, transfers guide data (to be described later) generated by the guide data generating circuitry 10 to the display circuitry 8.

If an instruction to generate Doppler spectrum data is entered from the input circuitry 11 in a scan operation, the central processing circuitry 1 controls the memory circuitry 7 to store a transmission angle and a focusing distance so that a transmission beam can be focused on the position where the Doppler spectrum data should be generated. The central processing circuitry 1 transfers the information on the transmission angle and focusing distance from the memory circuitry 7 to the guide data generating circuitry 10.

Figure 2:
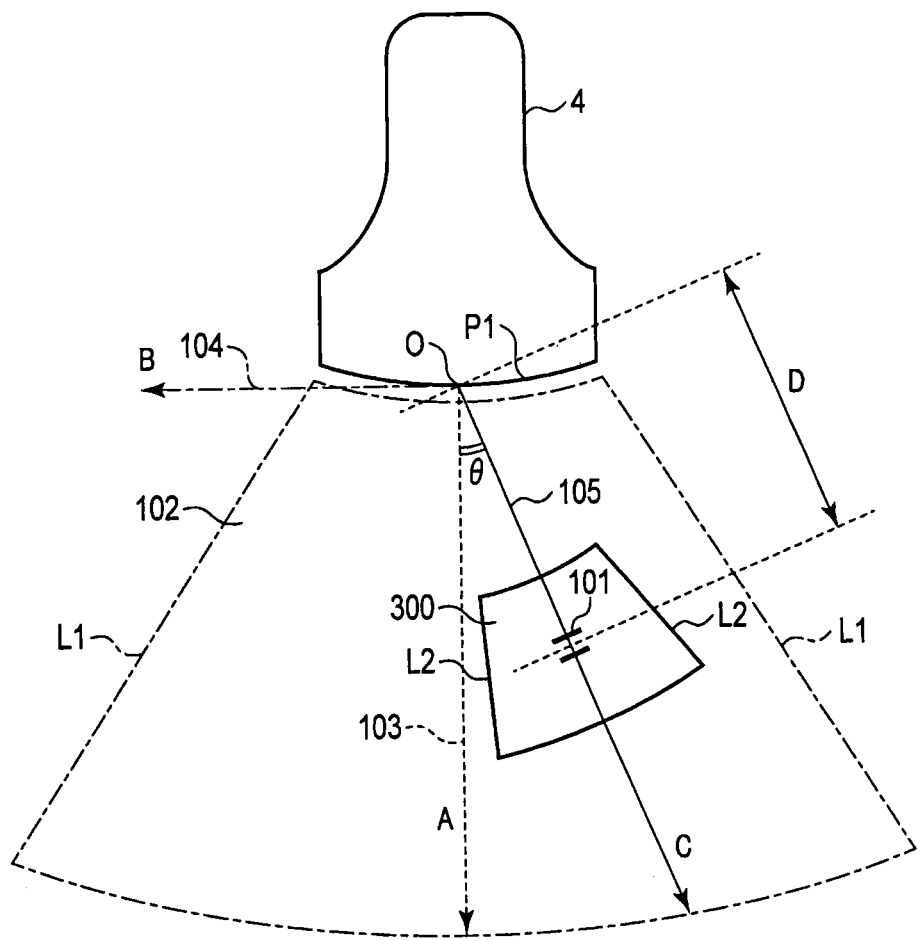
FIG. 2 is a schematic diagram illustrating a section of a B-mode image according to the embodiment.

FIG. 2 is a schematic diagram illustrating each scanning area. Arrow A, indicated by a broken line, shows the depth direction 103 of the ultrasonic probe. The depth direction 103 of the ultrasonic probe is perpendicular to transducer arrangement plane P1, which passes through a reference point O from which transmission beams are emitted. The reference point O is the center of an opening of the ultrasonic transducer in the B mode. For simplicity, a description will be given of the case where the reference point O is at the center of the distal end of the ultrasonic probe 4.

At the time of an ultrasonic scan, the ultrasonic probe 4 orientated in direction 103 is perpendicular to a patient. Arrow B, indicated by a two-chain line, shows a direction in which transducers are arranged (namely, transducer arrangement direction 104). In the B mode, scan plane 102 is a scanning area. The position information on the scan plane 102 is defined by the tilt angle and the scan angle of the scan plane. The tilt angle is a space between the scan plane relative and a normal line passing the reference point O, and perpendicular to the transducer arrangement plane P1. The scan angle is an angle formed by the scanning lines L1 at the respective ends of the scan plane. In the Doppler spectrum mode, range gates 101 on a scanning line 105 in the scan plane 102 determine a scanning area. The range gates 101 are indicated as two parallel markers (range gate markers) in a B-mode image regarding the scan plane 102. Arrow C, indicated by a solid line, indicates a traveling direction of a transmission beam corresponding to scanning line 105. The position information on the range gates 101 is defined by the transmission angle $\Theta$ of scanning line 105 and the depth D (focusing distance) of the range gates 101. The transmission angle $\Theta$ of scanning line 105 is defined by the angle of the scanning line relative to direction. A. The focusing distance D is a distance, as determined in direction C, between the transducer arrangement plane P1 and the range gates 101. In the color Doppler mode, a ROI 300 in the scan plane 102 is determined as a scanning area. The position information on the ROI 300 is defined by the transmission angles of the scanning lines L2 at the ends of the ROI 300. The position information on the ROI 300 may include a distance (depth) by which the ROI 300 is away from the transducer arrangement plane P1.

The central processing circuitry 1 controls the display circuitry 8 to show a predetermined operation menu.

The transmission/reception control circuitry 2 comprises a memory, not shown, and control data transferred by the central processing circuitry 1 is stored in the memory. The transmission/reception control circuitry 2 repeatedly generates a pulse signal at predetermined time intervals. A predetermined time interval is a unit time interval and will be referred to as a "rate" in the description below. A pulse signal which the transmission/reception control circuitry 2 generates in the rate will be referred to as a rate pulse. When one rate is started upon generation of a rate pulse, the transmission/reception control circuitry 2 selects control data related to the rate and supplies the selected control data to the transmission circuitry 3 and the reception circuitry 5.

The transmission circuitry 3 transmits a driving pulse based on the control data from the transmission/reception control circuitry 2 to the transducers of the ultrasonic probe 4.

The ultrasonic probe 4 is a convex type of probe provided with a plurality of transducers (not shown) arranged in one dimension. Each transducer generates an ultrasonic wave upon reception of the driving pulse from the transmission circuitry 3, and generates an echo signal upon reception of a reflection wave reflected by an internal tissue of a patient. The echo signal generated by each transducer is transmitted to the reception circuitry 5. The ultrasonic probe 4 is provided with a position sensor 201. The position sensor 201 senses the intensity of a magnetic field generated by a magnetic field generating circuitry 203 and transmits information indicative of the sensed intensity of the magnetic field to the position information acquiring circuitry 202. Based on the intensity information of the magnetic field received from the position sensor 201, the position information acquiring circuitry 202 acquires position information, including (i) coordinates of the ultrasonic probe 4 in a three-dimensional magnetic field coordinate system corresponding to a real space coordinate system in which the magnetic field generating circuitry 203 is used as a reference, (ii) the angle of the ultrasonic probe 4 in the rotating direction, (iii) the angle of the ultrasonic probe 4 in the depth direction (the rotating axis direction), etc.

Figure 3:
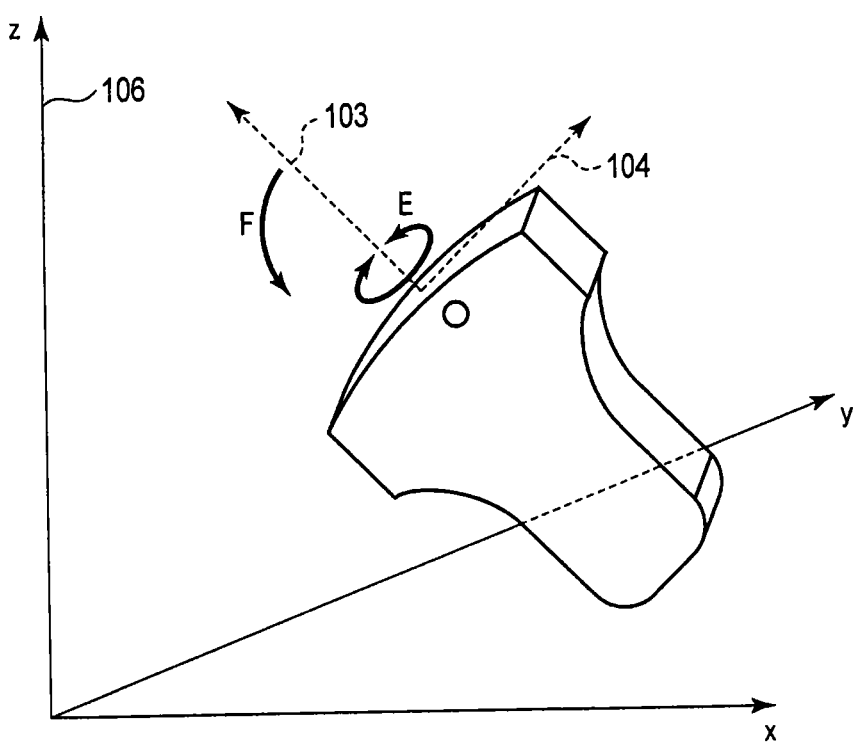
FIG. 3 is a conceptual diagram illustrating position information acquired by a position information acquiring circuitry of the embodiment.

FIG. 3 is a conceptual diagram illustrating position information acquired by the position information acquiring circuitry 202. As can be seen from FIG. 3, the position information acquiring circuitry 202 uses a three-dimensional magnetic field space coordinate system generated by the magnetic field generating circuitry 203. This coordinate system, hereinafter referred to as a position information acquiring circuitry coordinate system 106, is a coordinate system (x, y, z) defined by an x-axis, a y-axis and a z-axis. As shown in FIG. 3, the ultrasonic probe 4 is rotatable in the directions indicated by arrow E, and the depth direction coincident with the axis of rotation is rotated in the direction indicated by arrow F. In the present embodiment, the position information acquiring circuitry 202 acquires position information on the assumption that: the coordinates of position O, which is the center of the distal end of the ultrasonic probe 4 in the position information acquiring circuitry coordinate system 106, are the coordinates of the ultrasonic probe 4; the angle between the ultrasonic probe depth direction 103 and the positive direction of the x-axis is an angle of the ultrasonic probe 4 in the depth direction; and the angle between the transducer arrangement direction 104 and the position direction of the y-axis is an angle by which the ultrasonic probe 4 is rotated in the rotating direction. The absolute position of a scanning area is unconditionally determined based on the position information mentioned above and the position information on the scanning area. For example, the absolute position and direction of the range gates 201 are unconditionally determined based on the position information on the ultrasonic probe 4 and the transmission angle and focusing distance described above.

The reception circuitry 5 amplifies the signal intensity of an echo signal received from the ultrasonic probe 4 and performs phasing addition processing based on the control data. An echo signal subjected to the phasing addition processing is supplied to the signal processing circuitry 6.

The signal processing circuitry 6 executes signal processing for the echo signal received from the reception circuitry 5 in accordance with the scanning mode, and the signal subjected to the signal processing is transmitted to the memory circuitry 7. The signal processing executed by the signal processing circuitry 6 differs as described below, depending upon the scanning mode, namely, the B mode, the color Doppler mode and the Doppler spectrum mode.

In the B mode, the signal processing circuitry 6 executes envelope detecting processing and logarithmic compression processing with respect to the echo signal received from the reception circuitry 5, thereby generating a reception signal. The signal processing circuitry 6 generates B-mode data based on reception signals pertaining to all control data for B-mode data generation. The signal processing circuitry 6 transmits the generated B-mode data to the memory circuitry 7.

In the color Doppler mode, the signal processing circuitry 6 executes frequency analysis (e.g., an autocorrelation technique) with respect to the echo signal received from the reception circuitry 5, thereby detecting a frequency shift component included in the echo signal. The signal processing circuitry 6 acquires the detected frequency shift component as a Doppler signal. The signal processing circuitry 6 generates color Doppler data based on reception signals pertaining to all control data for color Doppler data generation. The signal processing circuitry 6 transmits the generated color Doppler data to the memory circuitry 7.

In the Doppler spectrum mode, the signal processing circuitry 6 executes frequency analysis (e.g., fast Fourier transform) with respect to the echo signal received from the reception circuitry 5, thereby detecting a frequency shift component included in the echo signal. The signal processing circuitry 6 acquires the detected frequency shift component as a Doppler signal. The signal processing circuitry 6 generates Doppler spectrum data at a position designated from the input circuitry 11, based on control data for Doppler spectrum data generation. The signal processing circuitry 6 transmits the generated Doppler spectrum data to the memory circuitry 7.

The memory circuitry 7 stores the B-mode data, color Doppler data and Doppler spectrum data received from the signal processing circuitry 6. In accordance with instructions from the central processing circuitry 1, the memory circuitry 7 transfers the B-mode data, color Doppler data and Doppler spectrum data to the display circuitry 8. In accordance with an instruction from the central processing circuitry 1, the memory circuitry 7 stores volume data transferred from the image server 200. In accordance with an instruction from the central processing circuitry 1, the memory circuitry 7 transfers the volume data to the display circuitry 8. The memory circuitry 7 transfers the volume data stored therein to the position information converting circuitry 9. In accordance with an instruction from the central processing circuitry 1, the memory circuitry 7 stores position information, acquired by the position information acquiring circuitry 202 and representing the position of the ultrasonic probe 4 in a past scan. In accordance with an instruction from the central processing circuitry 1, the memory circuitry 7 stores position information, acquired by the position information acquiring circuitry 202 and representing the position of the ultrasonic probe 4 in a current Doppler measurement. In accordance with an instruction from the central processing circuitry 1, the memory circuitry 7 transfers position information, acquired by the position information acquiring circuitry 202, to the position information converting circuitry 9. The memory circuitry 7 stores position information on the ultrasonic probe 4, which is transferred from the position information converting circuitry 9 and representing where the ultrasonic probe 4 is located in a volume data coordinate system. In accordance with an instruction from the central processing circuitry 1, the memory circuitry 7 transfers to the guide data generating circuitry 10 the position information on the ultrasonic probe 4, which is transferred from the position information converting circuitry 9 and representing where the ultrasonic probe 4 is located in the volume data coordinate system. In accordance with an instruction from the central processing circuitry 1, the memory circuitry 7 stores a transmission angle and a focusing distance used when the generation of Doppler spectrum data is designated in a past scan.

In accordance with an instruction from the central processing circuitry 1, the display circuitry 8 displays a predetermined operation menu. In accordance with instructions from the central processing circuitry 1, the display circuitry 8 displays the B-mode data, color Doppler data and Doppler spectrum data as images. In accordance with an instruction from the central processing circuitry 1, the display circuitry 8 displays guide data transferred from the guide data generating circuitry 10 as volume data.

The position information converting circuitry 9 converts the position information on the ultrasonic probe 4, which represents where the ultrasonic probe 4 was in a past scan based on the three-dimensional magnetic field space coordinate system transferred from the memory circuitry 7, into position information based on the volume data coordinate system transferred from the memory circuitry 7. The position information converting circuitry 9 converts the position information on the ultrasonic probe 4, which represents where the ultrasonic probe 4 is located in a current or live scan based on the three-dimensional magnetic field space coordinate system transferred from the memory circuitry 7, into position information based on the volume data coordinate system transferred from the memory circuitry 7. The position information converting circuitry 9 transfers the position information on the ultrasonic probe 4, which is position information based on the volume data coordinate system, to the memory circuitry 7 again. The position information converting circuitry 9 transfers the position information on the ultrasonic probe 4, which is position information based on the volume data coordinate system, to the guide data generating circuitry 10. Details of the position information converting circuitry 9 will be described later.

The guide data generating circuitry 10 generates guide data based on the position information on the ultrasonic probe 4, which is transferred from the position information converting circuitry 9 and representing where the ultrasonic probe 4 is located in the volume data coordinate system. The guide data generating circuitry 10 generates guide data based on the position information on the ultrasonic probe 4, which is transferred from the memory circuitry 7 and represents where the ultrasonic probe 4 is located in the volume data coordinate system, and the transmission angle and focusing distance transferred from the memory circuitry 7. The guide data generating circuitry 10 generates guide data based on the position information on the ultrasonic probe 4, which is transferred from the position information converting circuitry 9 and represents where the ultrasonic probe 4 is located in the volume data coordinate system, and the transmission angle and focusing distance transferred from the memory circuitry 7. In accordance with an instruction from the central processing circuitry 1, the guide data generating circuitry 10 transfers the generated guide data to the display circuitry 8. Details of the guide data will be described later.

The input circuitry 11 is, for example, a track ball, a keyboard, or a touch panel configured as a display circuitry 8 as well. The operator performs an operation shown on the predetermined operation menu on the display circuitry 8, by operating the input circuitry 11.

Figure 4:
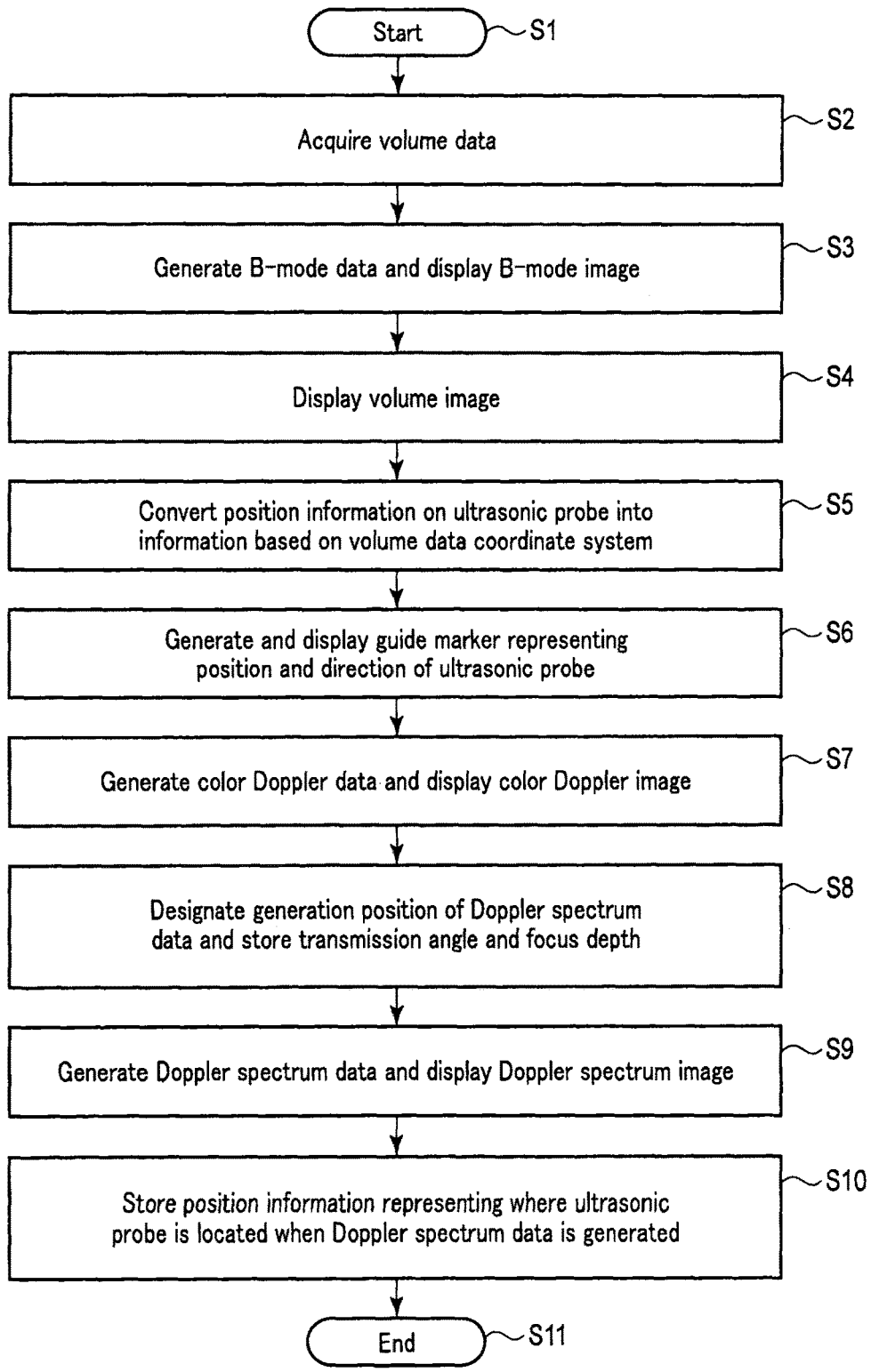
FIG. 4 is a flowchart illustrating the first examination of a follow-up according to the embodiment.
Figure 5:
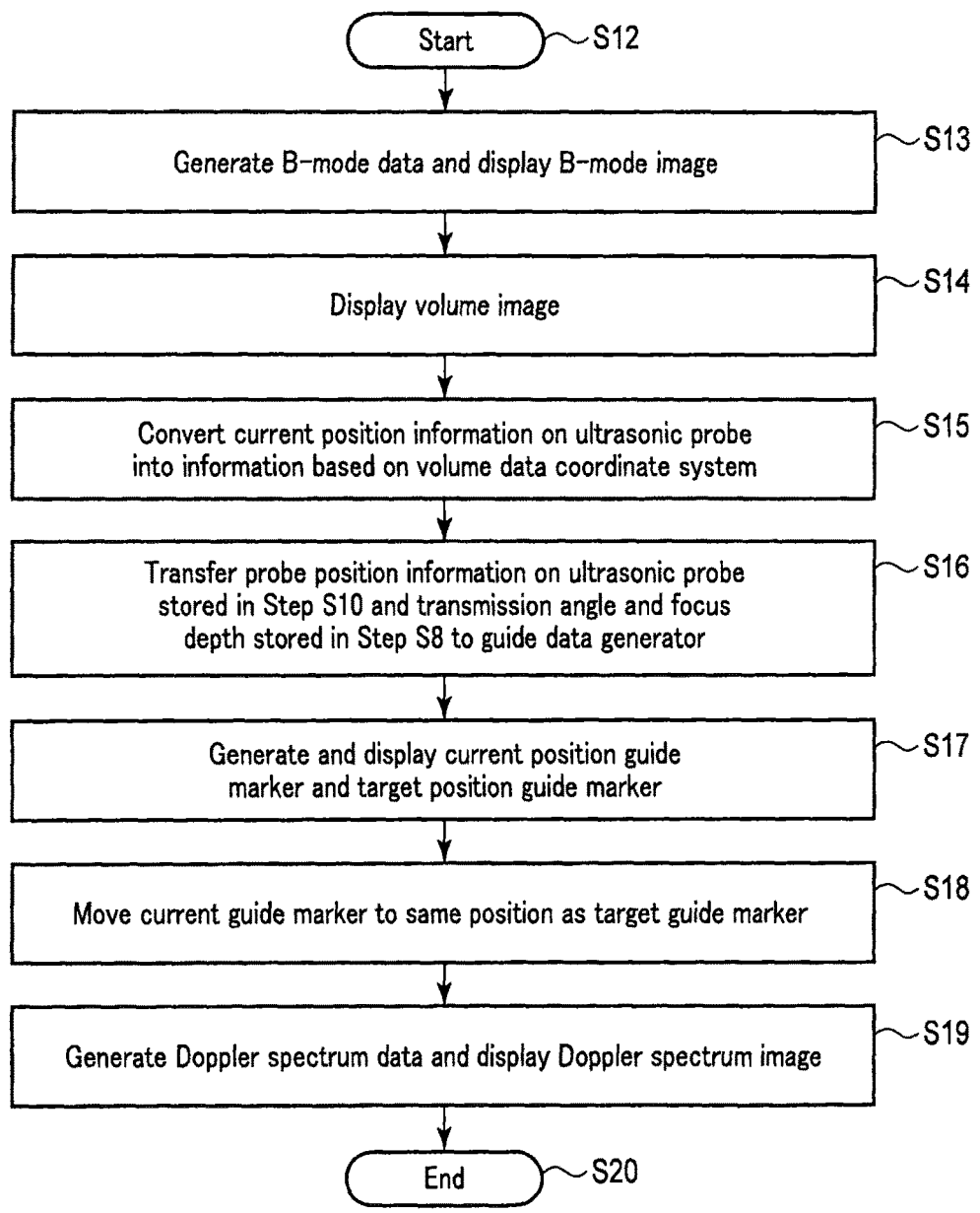
FIG. 5 is a flowchart illustrating the second and subsequent checks according to the embodiment.

Next, an operation performed by the ultrasonic diagnostic apparatus 100 of the present embodiment will be described with reference to the flowcharts shown in FIGS. 4 and 5. An operation described with reference to FIGS. 4 and 5 is performed for examining the flow velocity of a patient in a follow-up. FIG. 4 illustrates a first examination of the follow-up, and FIG. 5 illustrates second and subsequent examinations of the follow-up. In the present embodiment, the position information acquiring circuitry 202 constantly acquires the position information on the ultrasonic probe, and the central processing circuitry 1 controls the memory circuitry 7 to store, at proper intervals, the position information acquired by the position information acquiring circuitry 202. The position information on the ultrasonic probe 4 will be referred to as probe position information.

First, a description will be given of how the first examination of a follow-up is performed, referring to the flowchart shown in FIG. 4.

In Step S1, the operator starts diagnosis.

In Step S2, the operator operates the input circuitry 11 and enters an instruction to the central processing circuitry 1 so that volume data including data at the position to be followed up is acquired from the image server 200. In accordance with instructions from the input circuitry 11, the central processing circuitry 1 transfers the volume data, including data at the position to be followed up, from the image server 200 to the memory circuitry 7, and records the volume data in the memory circuitry 7. If there is a planned diagnostic schedule, the volume data on a patient may be transferred from the image server 200 in advance before the start of the diagnosis.

In Step S3, the operator operates the input circuitry 11 and enters an instruction to the central processing circuitry 1 so as to generate B-mode data. In accordance with an instruction from the input circuitry 11, the central processing circuitry 1 generates control data used for generating B-mode data, and transfers the B-mode-data-generation control data to the transmission/reception control circuitry 2. The transmission/reception control circuitry 2 controls its memory circuitry means to store control data transferred from the central processing circuitry 1. When one rate is started upon generation of a rate pulse, the transmission/reception control circuitry 2 selects control data related to the rate and supplies the selected control data to the transmission circuitry 3. The transmission circuitry 3 transmits a driving pulse based on the control data from the transmission/reception control circuitry 2 to the transducers of the ultrasonic probe 4. Each of the transducers of the ultrasonic probe 4 generates an ultrasonic wave upon reception of the driving pulse from the transmission circuitry 3, and generates an echo signal upon reception of a reflection wave reflected by an internal tissue of the patient. Each of the transducers transmits the generated echo signal to the reception circuitry 5. Upon reception of the echo signal, the reception circuitry 5 amplifies the signal intensity of the echo signal and performs phasing addition processing based on the control data. At the end of the phasing addition processing, the reception circuitry 5 transmits the echo signal to the signal processing circuitry 6. The signal processing circuitry 6 executes envelope detecting processing and logarithmic compression processing with respect to the echo signal, thereby generating a reception signal. The signal processing circuitry 6 generates B-mode data based on reception signals pertaining to all control data for B-mode data generation, and supplies the generated B-mode data to the memory circuitry 7. The memory circuitry 7 stores the B-mode data received from the signal processing circuitry 6. The operator operates the input circuitry 11 and enters an instruction to the central processing circuitry 1 so as to transfer the B-mode data stored in the memory circuitry 7 to the display circuitry 8. In accordance with an instruction from the input circuitry 11, the central processing circuitry 1 transfers the B-mode data from the memory circuitry 7 to the display circuitry 8. The display circuitry 8 displays the B-mode data transferred from the memory circuitry 7, as a B-mode image.

In Step S4, the operator operates the input circuitry 11 and enters an instruction to the central processing circuitry 1 so that the volume data stored in the memory circuitry 7 can be displayed on the display circuitry 8. In accordance with an instruction from the input circuitry 11, the central processing circuitry 1 transfers the volume data from the memory circuitry 7 to the display circuitry 8. In accordance with an instruction from the central processing circuitry 1, the display circuitry 8 displays an image based on the volume data transferred from the memory circuitry 7. A display image based on the volume data will be hereinafter referred to as "volume image." The volume image is generated by executing three-dimensional image processing to the volume data by the central processing circuitry 1. The three-dimensional image processing includes volume rendering, surface rendering, multi-planar reconstruction (MPR), curved planer reconstruction (CPR), projection processing, or the like.

In Step S5, the operator operates the input circuitry 11 and enters an instruction to the central processing circuitry 1 so that the probe position information can be converted into information based on the volume data coordinate system. In accordance with an instruction from the input circuitry 11, the central processing circuitry 1 transfers the volume data from the memory circuitry 7 to the position information converting circuitry 9. The central processing circuitry 1 transfers the position information on the ultrasonic probe 4, stored in the memory circuitry 7 at proper intervals, to the position information converting circuitry 9. The position information converting circuitry 9 converts the probe position information transferred from the memory circuitry 7 into position information based on the volume data coordinate system transferred from the memory circuitry 7. The position information converting circuitry 9 transfers the position information, which is position information based on the volume data coordinate system, to the guide data generating circuitry 10.

Figure 6:
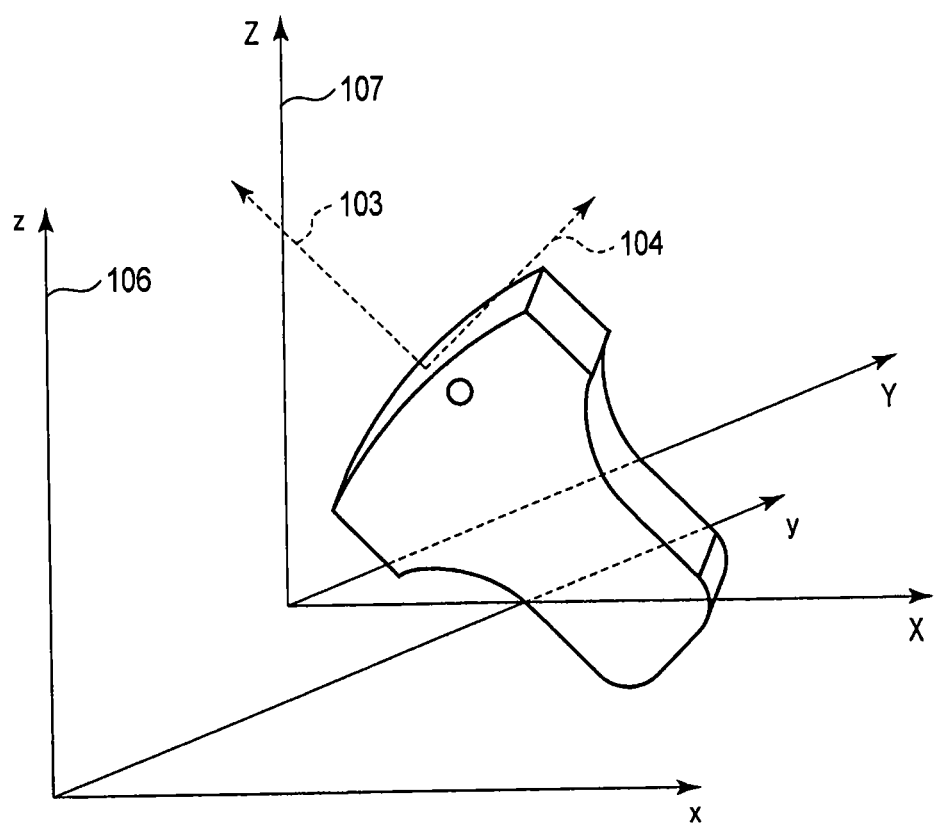
FIG. 6 is a conceptual diagram illustrating how the position information acquired by the position information acquiring circuitry of the embodiment is converted.

FIG. 6 is a conceptual diagram illustrating how the position information is converted by the position information converting circuitry 9. As shown in FIG. 6, the coordinate system for the volume data (volume data coordinate system 107) is, for example, an XYZ Cartesian coordinate system (X, Y, Z) that expresses data using an X-axis, a Y-axis and a Z-axis. It is assumed that the volume data coordinate system 107 is a coordinate system that is shifted from the position information acquiring circuitry coordinate system 106, by +a in the x-axis direction, by +b in the y-axis direction and by +c in the z-axis direction. It is also assumed that the coordinates of the reference point O in the position information acquiring circuitry coordinate system 106 are (x0, y0, z0). In this case, the coordinates of the reference point O in the volume data coordinate system 107 are converted to (x0-a, y0-b, z0-c). In the above example, the volume data coordinate system 107 is not a coordinate system obtained by rotating the position information acquiring circuitry coordinate system 106. Therefore, the ultrasonic probe depth direction 103 and the transducer arrangement direction 104 remain unchanged. Where the volume data coordinate system 107 is a coordinate system obtained by rotating the position information acquiring circuitry coordinate system 106, the coordinate conversion is performed in a similar manner.

In Step S6, the guide data generating circuitry 10 generates guide data, which represents current probe position information based on the volume data coordinate system 107. The guide data generating circuitry 10 transfers the guide data to the display circuitry 8. The display circuitry 8 displays guide data, representing probe position information, as a guide marker on a volume image. In the description below, the guide marker representing the probe position information will be referred to as a "probe marker."

Figure 7A:
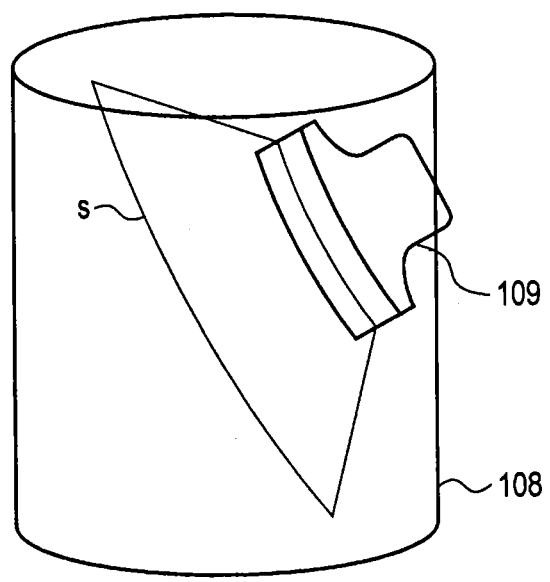
FIG. 7A is a schematic diagram illustrating a B-mode image according to the embodiment.
Figure 7B:
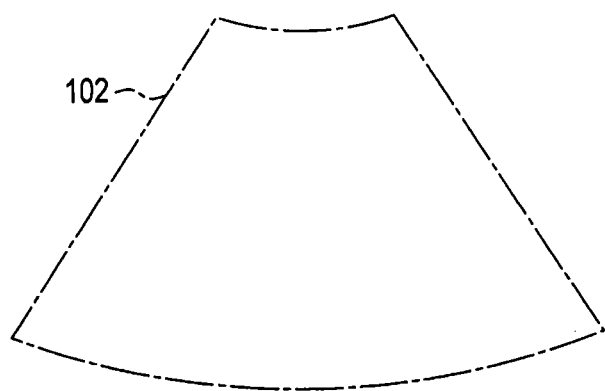
FIG. 7B is a schematic diagram illustrating a volume image according to the embodiment.

FIG. 7A is a schematic diagram illustrating a B-mode image 102 displayed on the display circuitry 8. FIG. 7B is a schematic diagram illustrating a volume image 108 displayed on the display circuitry 8. As shown in FIGS. 7A and 7B, the probe marker 109 indicative of the current position information on the ultrasonic probe 4 is displayed on the volume image 108. The display circuitry 8 displays the probe marker 109 and the volume image 108, with their positions being determined based on the probe position information regarding the probe marker 109. In order to enable the operator to clearly understand where the current B-mode scanning plane is, the display circuitry 8 may be configured to display a marker S indicative of the scan plane, with its position determined with reference to the probe marker 109. In the description below, the marker S indicative of the scanning plane will be referred to as a scan plane marker S. The display position and direction of the scan plane marker S are determined based on the current position information on the ultrasonic probe 4 and the position information on the B-mode scan plane. The display position and direction of the scan plane marker S correspond to the spatial position and direction of the plane of the B-mode image 102 acquired actually and displayed in real time. The probe marker 109 and the scan plane marker S may be superimposed on the volume image 108 when they are displayed. In order to enable clear understanding of how the probe marker 109 and the scan plane marker S are positioned and orientated with reference to an internal organ of a patient, the display circuitry 8 may be configured to display the volume image 10, with the body surface part of the volume image 108 being shown with an appropriate degree of transparency. The position and direction of the probe marker 109 are updated at proper intervals in accordance with the position information acquired by the position information acquiring circuitry 202.

In Step S7, the operator confirms that the scanning area of the B-mode image 102 includes a target for which a color Doppler scan is to be performed, and upon confirmation of this, the operator operates the input circuitry 11 to designate a color Doppler data generation range in the B-mode image 102 displayed on the display circuitry 8 and enters an instruction to generate color Doppler data to the central processing circuitry 1. In accordance with an instruction from the input circuitry 11, the central processing circuitry 1 generates control data used for generating color Doppler data in the range designated with the input circuitry 11, and transfers the color-Doppler-data-generation control data to the transmission circuitry 3. The transmission/reception control circuitry 2 controls its memory circuitry means to store the color-Doppler-data-generation control data transferred from the central processing circuitry 1. When one rate is started upon generation of a rate pulse, the transmission/reception control circuitry 2 selects control data related to the rate from the color-Doppler-data-generation control data and supplies the selected control data to the transmission circuitry 3. The transmission circuitry 3 transmits a driving pulse based on the control data received from the transmission/reception control circuitry 2 to the transducers of the ultrasonic probe 4. Each of the transducers of the ultrasonic probe 4 generates an ultrasonic wave upon reception of the driving pulse from the transmission circuitry 3, and generates an echo signal upon reception of a reflection wave reflected by an internal tissue of the patient. Each of the transducers transmits the generated echo signal to the reception circuitry 5. Upon reception of the echo signal, the reception circuitry 5 amplifies the signal intensity of the echo signal and performs phasing addition processing based on the control data. At the end of the phasing addition processing, the reception circuitry 5 transmits the echo signal to the signal processing circuitry 6. The signal processing circuitry 6 detects a frequency shift occurred in the echo signal by an autocorrelation technique, as frequency analysis of the echo signal. The signal processing circuitry 6 acquires the detected frequency shift as a Doppler signal. The signal processing circuitry 6 generates color Doppler data corresponding to the range designated with the input circuitry 11, based on all control data for color Doppler data generation, and transmits the generated color Doppler data to the memory circuitry 7. The memory circuitry 7 stores the color Doppler data received from the signal processing circuitry 6. The operator operates the input circuitry 11 and enters an instruction to the central processing circuitry 1 so as to transfer the color Doppler data stored in the memory circuitry 7 to the display circuitry 8. In accordance with an instruction from the input circuitry 11, the central processing circuitry 1 transfers the color Doppler data from the memory circuitry 7 to the display circuitry 8. The display circuitry 8 displays the color Doppler data transferred from the memory circuitry 7 as a color Doppler image, with the color Doppler data being superimposed on the B-mode image 102.

In Step S8, the operator confirms that the scanning area of the color Doppler image includes a target for which Doppler spectrum measurement is to be performed, and upon confirmation of this, the operator operates the input circuitry 11 to designate a Doppler spectrum data generation position, namely, a range gate display position, in the color Doppler image displayed on the display circuitry 8. The central processing circuitry 1 controls the display circuitry 8 to display range gate markers. The display circuitry 8 displays range gate markers at the designated display position. The central processing circuitry 1 calculates a transmission angle and a focusing distance that enable a transmission beam to be focused on the designated display position in the current arrangement of the ultrasonic probe 4. The calculated transmission angle and focusing distance will be referred to as transmission angle and focusing distance for a first examination (past examination). The central processing circuitry 1 controls the memory circuitry 7 to store the transmission angle and the focusing distance of the first examination.

In Step S9, the operator enters an instruction to the central processing circuitry 1 so as to generate Doppler spectrum data. In accordance with an instruction from the input circuitry 11, the central processing circuitry 1 generates control data used for generating Doppler spectrum data at the position designated with the input circuitry 11, and transfers the Doppler-spectrum-data-generation control data to the transmission circuitry 3. The transmission/reception control circuitry 2 controls its memory circuitry means to store the Doppler-spectrum-data-generation control data transferred from the central processing circuitry 1. When one rate is started upon generation of a rate pulse, the transmission/reception control circuitry 2 selects control data related to the rate from the Doppler-spectrum-data-generation control data and supplies the selected control data to the transmission circuitry 3. The transmission circuitry 3 transmits a driving pulse based on the control data received from the transmission/reception control circuitry 2 to the transducers of the ultrasonic probe 4. Each of the transducers of the ultrasonic probe 4 generates an ultrasonic wave upon reception of the driving pulse from the transmission circuitry 3, and generates an echo signal upon reception of a reflection wave reflected by an internal tissue of the patient. Each of the transducers transmits the generated echo signal to the reception circuitry 5. Upon reception of the echo signal, the reception circuitry 5 amplifies the signal intensity of the echo signal and performs phasing addition processing based on the control data. At the end of the phasing addition processing, the reception circuitry 5 transmits the echo signal to the signal processing circuitry 6. The signal processing circuitry 6 detects a frequency shift occurred in the echo signal by fast Fourier transform, as frequency analysis of the echo signal. The signal processing circuitry 6 acquires the detected frequency shift as a Doppler signal. The signal processing circuitry 6 generates Doppler spectrum data at a position designated by the input circuitry 11, based on control data for Doppler spectrum data generation, and supplies the generated Doppler spectrum data to the memory circuitry 7. The memory circuitry 7 stores the Doppler spectrum data received from the signal processing circuitry 6. The operator operates the input circuitry 11 and enters an instruction to the central processing circuitry 1 so as to transfer the Doppler spectrum data stored in the memory circuitry 7 to the display circuitry 8. In accordance with an instruction from the input circuitry 11, the central processing circuitry 1 transfers the Doppler spectrum data from the memory circuitry 7 to the display circuitry 8. The display circuitry 8 displays the Doppler spectrum data transferred from the memory circuitry 7, as a Doppler spectrum image.

In Step S10, when the operator finishes observing the Doppler spectrum image, the central processing circuitry 1 transfers, to the position information converting circuitry 9, the probe position information that is stored in the memory circuitry 7 when the operator operates the input circuitry 11 and enters an instruction to generate the Doppler spectrum data to the central processing circuitry 1. The position information converting circuitry 9 converts the probe position information transferred from the memory circuitry 7 into position information based on the volume data coordinate system. In the descriptions below, the probe position information expressed in the volume data coordinate system generated in Step S10 will be referred to as probe position information of the first examination. The position information converting circuitry 9 transfers the probe position information of the first examination to the memory circuitry 7. The memory circuitry 7 stores the probe position information of the first examination transferred from the position information converting circuitry 9.

In Step S11, the operator ends the diagnosis.

A description will be given of the second and subsequent examinations of the follow-up shown in FIG. 5. It is assumed that in the second and subsequent examinations, the operator performs Doppler spectrum measurement at the same position as the first Doppler spectrum measurement.

In Step S12, the operator starts diagnosis.

In Step S13, the operator operates the input circuitry 11 and enters an instruction to the central processing circuitry 1 so as to generate B-mode data. In accordance with an instruction from the input circuitry 11, the central processing circuitry 1 generates control data used for generating B-mode data, and transfers the B-mode-data-generation control data to the transmission/reception control circuitry 2. The transmission/reception control circuitry 2 controls its memory circuitry means to store control data transferred from the central processing circuitry 1. When one rate is started upon generation of a rate pulse, the transmission/reception control circuitry 2 selects control data related to the rate and supplies the selected control data to the transmission circuitry 3. The transmission circuitry 3 transmits a driving pulse based on the control data received from the transmission/reception control circuitry 2 to the transducers of the ultrasonic probe 4. Each of the transducers of the ultrasonic probe 4 generates an ultrasonic wave upon reception of the driving pulse from the transmission circuitry 3, and generates an echo signal upon reception of a reflection wave reflected by an internal tissue of the patient. Each of the transducers transmits the generated echo signal to the reception circuitry 5. Upon reception of the echo signal, the reception circuitry 5 amplifies the signal intensity of the echo signal and performs phasing addition processing based on the control data. At the end of the phasing addition processing, the reception circuitry 5 transmits the echo signal to the signal processing circuitry 6. The signal processing circuitry 6 executes envelope detecting processing and logarithmic compression processing with respect to the echo signal, thereby generating a reception signal. The signal processing circuitry 6 generates B-mode data based on reception signals pertaining to all control data for B-mode data generation, and supplies the generated B-mode data to the memory circuitry 7. The memory circuitry 7 stores the B-mode data received from the signal processing circuitry 6. The operator operates the input circuitry 11 and enters an instruction to the central processing circuitry 1 so as to transfer the B-mode data stored in the memory circuitry 7 to the display circuitry 8. In accordance with an instruction from the input circuitry 11, the central processing circuitry 1 transfers the B-mode data from the memory circuitry 7 to the display circuitry 8. The display circuitry 8 displays the B-mode data transferred from the memory circuitry 7, as a B-mode image.

In Step S14, the central processing circuitry 1 controls the display circuitry 8 to display an image data list stored in the memory circuitry 7 as a predetermined operation menu. The operator operates the input circuitry 11 to select the volume data stored in the memory circuitry 7 from the list. The central processing circuitry 1 transfers the volume data selected by the operator from the memory circuitry 7 to the display circuitry 8. In accordance with an instruction from the central processing circuitry 1, the display circuitry 8 displays a volume image based on the volume data transferred from the memory circuitry 7.

In Step S15, the operator operates the input circuitry 11 and enters an instruction to the central processing circuitry 1 so that the current probe position information can be converted into information based on the volume data coordinate system. In accordance with an instruction from the input circuitry 11, the central processing circuitry 1 first transfers the volume data from the memory circuitry 7 to the position information converting circuitry 9. Then, the central processing circuitry 1 transfers the position information, stored in the memory circuitry 7 at proper intervals, to the position information converting circuitry 9. The position information converting circuitry 9 converts the probe position information transferred from the memory circuitry 7 into position information based on the volume data coordinate system transferred from the memory circuitry 7. The position information converting circuitry 9 transfers the position information, which is position information based on the volume data coordinate system, to the guide data generating circuitry 10.

In Step S16, the central processing circuitry 1 transfers (i) the probe position information of the first examination stored in the memory circuitry 7 in Step S10 and (ii) the information on the transmission angle and focusing distance of the first examination stored in the memory circuitry in Step S8, to the guide data generating circuitry 10.

In Step S17, the guide data generating circuitry 10 generates guide data based on the current probe position information and the transmission angle and focusing distance of the first examination. In the descriptions below, this guide data will be referred to as current guide data. The guide data generating circuitry 10 generates guide data based on the probe position information of the first examination and the transmission angle and focusing distance of the first examination. The guide data on the first examination is used in the second and subsequent examinations of the follow-up as data representing the target positions of the ultrasonic probe 4 and the range gates. In the descriptions below, this guide data will be referred to as target guide data. The guide data generating circuitry 10 transfers the current guide data and the target guide data to the display circuitry 8. The display circuitry 8 displays the current guide data and the target guide data as guide markers.

Figure 8:
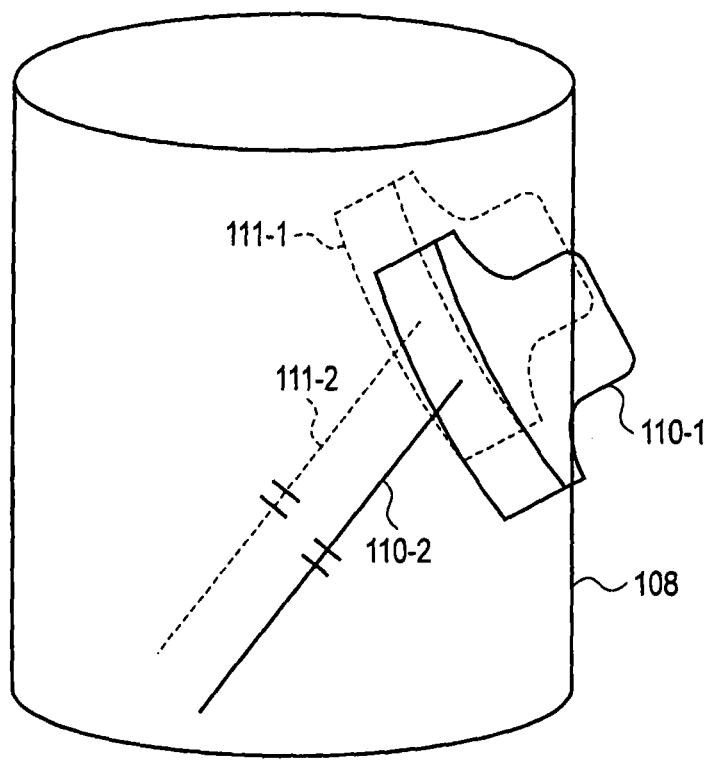
FIG. 8 is a schematic diagram illustrating a current guide marker and a target guide marker according to the embodiment.

FIG. 8 shows guide markers displayed on the display circuitry 8 in Step S17. In Step S17, the display circuitry 8 displays a current guide marker 110 corresponding to the current guide data and a target guide marker 111 corresponding to the target guide data, with the positions of the markers being determined in relation to each other. The current guide marker 110 includes a current probe marker 110-1 representing the current ultrasonic probe 4 and a range gate guide marker 110-2 representing the scanning line and range gates of the first examination. The target guide marker 111 includes a target probe marker 111-1 representing the ultrasonic probe 4 of the first examination and a target range gate guide marker 111-2 representing the scanning line and range gates of the first examination. The display circuitry 8 displays the current probe marker 110-1 on the volume image 108, based on the current probe position information and in accordance with the position and direction of the current ultrasonic probe 4. The display circuitry 8 displays the current range gate guide marker 110-2 on the volume image 108, based on the transmission angle and focusing distance of the first examination and in accordance with the position and direction of the range gates of the first examination. At the time, the display circuitry 8 displays the base portion of the current range gate guide marker 110-2 at the position corresponding to the reference point O of the current probe marker 110-1.

Likewise, the display circuitry 8 displays the target probe marker 110-1 on the volume image 108, based on the probe position information of the first examination and in accordance with the position and direction of the ultrasonic probe 4 of the first examination. The display circuitry 8 displays the target range gate guide probe marker 110-2 on the volume image 108, based on the transmission angle and focusing distance of the first examination and in accordance with the position and direction of the range gates of the first examination. At the time, the display circuitry 8 displays the base portion of the target range gate guide marker 110-2 at the position corresponding to the reference point O of the target probe marker 110-1. In order to enable clear understanding of how the range gate markers 110-2 and 111-2 are positioned and orientated with reference to an internal organ of a patient, the display circuitry 8 may be configured to display the volume image 10, with the body surface part of the volume image 108 being shown with an appropriate degree of transparency. In addition, the display circuitry 8 may be configured to display the current guide marker 110 and the target guide marker 111 in different manners, for easy distinction between them. For example, the display circuitry 8 may be configured to display the current guide marker 110 and the target guide marker 111 in different colors or with different kinds of line. Alternatively, one of the current guide marker 110 and the target guide marker 111 may be displayed to blink.

The operator changes the position and direction of the ultrasonic probe 4 pressed against the patient, in such a manner that the current guide marker 110 displayed on the display circuitry 8 is on the target guide marker 111. The position and direction of the current guide marker 110 are updated at proper intervals in accordance with the position information acquired by the position information acquiring circuitry 202.

In Step S18, the operator operates the ultrasonic probe 4 so that the current guide marker 110 is displayed on the same position as the target guide marker 111.

After the target guide marker 111 and the current guide marker 110 are displayed at the same position, Step S19 is executed, in which the central processing circuitry 1 determines the position of the range gate marker in accordance with the transmission angle and focusing distance stored in the memory circuitry 7 in Step S8, and generates Doppler spectrum data. In other words, when the operator moves the ultrasonic probe 4 in such a manner that the current guide marker 110 is displayed at the same position as the target guide marker 111, the generation of Doppler spectrum data is automatically started. In accordance with an instruction from the input circuitry 11, the central processing circuitry 1 generates control data used for generating Doppler spectrum data at the position designated with the input circuitry 11, and transfers the Doppler-spectrum-data-generation control data to the transmission circuitry 3. The transmission/reception control circuitry 2 controls its memory circuitry means to store the Doppler-spectrum-data-generation control data transferred from the central processing circuitry 1. When one rate is started upon generation of a rate pulse, the transmission/reception control circuitry 2 selects control data related to the rate from the Doppler-spectrum-data-generation control data and supplies the selected control data to the transmission circuitry 3. The transmission circuitry 3 transmits a driving pulse based on the control data received from the transmission/reception control circuitry 2 to the transducers of the ultrasonic probe 4. Each of the transducers of the ultrasonic probe 4 generates an ultrasonic wave upon reception of the driving pulse from the transmission circuitry 3, and generates an echo signal upon reception of a reflection wave reflected by an internal tissue of the patient. Each of the transducers transmits the generated echo signal to the reception circuitry 5. Upon reception of the echo signal, the reception circuitry 5 amplifies the signal intensity of the echo signal and performs phasing addition processing based on the control data. At the end of the phasing addition processing, the reception circuitry 5 transmits the echo signal to the signal processing circuitry 6. The signal processing circuitry 6 detects a frequency shift occurred in the echo signal by fast Fourier transform, as frequency analysis of the echo signal. The signal processing circuitry 6 acquires the detected frequency shift as a Doppler signal. The signal processing circuitry 6 generates Doppler spectrum data at a position designated by the input circuitry 11, based on control data for Doppler spectrum data generation, and supplies the generated Doppler spectrum data to the memory circuitry 7. The memory circuitry 7 stores the Doppler spectrum data received from the signal processing circuitry 6. The operator operates the input circuitry 11 and enters an instruction to the central processing circuitry 1 so as to transfer the Doppler spectrum data stored in the memory circuitry 7 to the display circuitry 8. In accordance with an instruction from the input circuitry 11, the central processing circuitry 1 transfers the Doppler spectrum data from the memory circuitry 7 to the display circuitry 8. The display circuitry 8 displays the Doppler spectrum data transferred from the memory circuitry 7, as a Doppler spectrum image.

After observing the Doppler spectrum, the operator ends the diagnosis in Step S20.

As described above, the ultrasonic diagnostic apparatus 100 of the present embodiment displays the current guide marker 110 (which is based on the probe position information constantly updated) on the volume image shown on the display circuitry 8, and further displays the target guide marker 111 (representing the probe position where the flow velocity was measured in the past). The operator changes the position and direction of the ultrasonic probe 4 in such a manner that the current guide marker 110 is displayed at the same position as the target guide marker 111. By virtue of this, the ultrasonic probe 4, with which to measure the flow velocity, can be adjusted to the position where measurement was performed in the past. In addition to the above, the ultrasonic diagnostic apparatus 100 of the present embodiment generates Doppler spectrum data, using the same the transmission angle and focusing distance as were used in the past measurement of the flow velocity. Because of this, the angle of the ultrasonic transmission/reception direction, as determined with reference to the blood flow direction, never fails to be the same angle as in the past measurement, and the reproducibility in diagnosis is ensured. Furthermore, the ultrasonic diagnostic apparatus 100 of the present embodiment provides improved reproducibility of diagnosis by the simple operation of displaying guide markers based on the probe position information at the same position on the display circuitry 8. Therefore, the present embodiment enables accurate diagnosis without reference to the operator's skills.

As a modification of the present embodiment, the target guide marker 111 and current guide marker 110 displayed on the volume image may be used in combination with a marker which represents the moving direction of the ultrasonic probe 4 and which enables the current guide marker 110 to be displayed at the same position as the target guide marker 111. This marker is, for example, an arrow marker, and indicates the direction in which the ultrasonic probe 4 should be moved.

In addition, the degree of matching between the current prove position information and the past probe position information may be calculated and displayed on the display circuitry 8. For example, the degree of matching may be a degree of matching regarding angles. If the ultrasonic probe depth direction 103 and transducer arrangement direction 104 in a current measurement are 180-degree opposite to those used in a past measurement, the degree of matching is assumed to be 0%. If the ultrasonic probe depth direction 103 and transducer arrangement direction 104 in the current measurement are the same as those used in the past measurement, the degree of matching is assumed to be 100%. Alternatively, the degree of matching may be a degree of matching regarding distances. Let us assume that a sphere has a radius R and a coordinate center O which is on the ultrasonic probe 4 used for measuring the flow velocity. If point O of the current ultrasonic probe 4 is at the center of the sphere, namely, if the coordinates of point O used when the ultrasonic probe 4 measured a flow velocity are the same as the coordinates of point O used when the ultrasonic probe 4 is measuring a flow velocity, then the degree of matching is assumed to be 100%. If the coordinates of point O of the current ultrasonic probe 4 are on the surface of the sphere, then the degree of matching is assumed to be 0%. If the coordinates of point O of the current ultrasonic probe 4 are out of the sphere, then no degree of matching is displayed. Alternatively, both the degree of matching regarding angles and the degree of matching regarding distances may be displayed.

Thanks to these, the operator can easily adjust the current position of the ultrasonic probe 4 to the past position.

The image based on the Doppler spectrum data generated in Step S19 need not be displayed solely; it may be displayed side by side with the image based on the Doppler spectrum data generated in Step S9 (i.e., in the first examination of a follow-up), for easy comparison.

Figure 9:
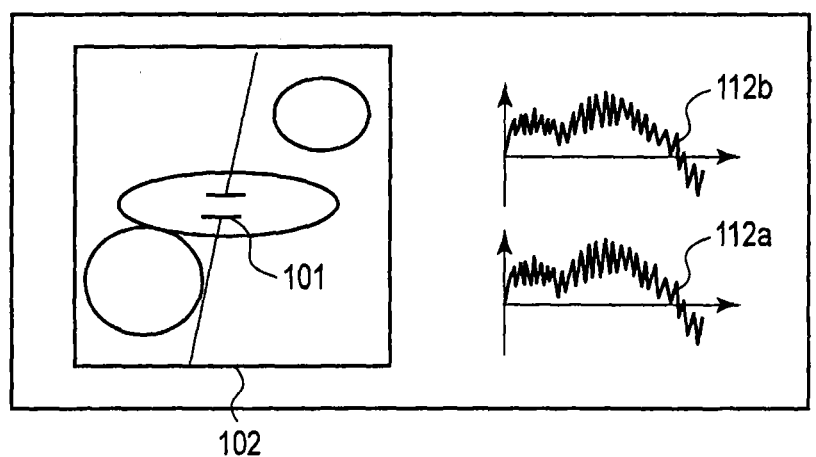
FIG. 9 is a schematic diagram illustrating a Doppler spectrum image according to the embodiment.

FIG. 9 is a schematic diagram illustrating a Doppler spectrum image 102 displayed on the display circuitry 8. In FIG. 9, the display circuitry 8 displays both the Doppler spectrum image 112a based on the Doppler spectrum data generated in the first examination of a follow-up and the Doppler spectrum image 112b based on the Doppler spectrum data generated, for example, in the second examination of the follow-up.

In addition, the display circuitry 8 may display maximum and average values of the flow velocity measured in Steps S9 and S19.

This enables the operator to confirm based on measurement results whether the position and direction of the current ultrasonic probe 4 are the same as those used in the first examination of a follow-up.

In connection with the present embodiment, reference was made to the case where the target guide marker 111 and the current guide marker 110 are displayed on the volume image. However, the target guide marker 111 and the current guide marker 110 may be displayed on a B-mode image.

FIG. 10 is a schematic diagram showing the current guide marker 110 and the target guide marker 111 displayed on the B-mode image 102. In the case of FIG. 10, the probe position information representing where a past blood flow measurement was effected and the probe position information representing where a current blood flow measurement is effected (both the probe position formation are expressed in the volume data coordinate system by the position information converting circuitry 9) are converted again into information expressed in the coordinate system of the current probe position information, and the current guide marker 110 and the target guide marker are displayed on the B-mode image 102 based on the position information obtained after the second conversion.

In connection with the present embodiment, reference was made to the case where the ultrasonic probe is an one-dimensional array probe wherein a plurality of transducers are arranged in one dimension. In place of this type of ultrasonic probe, a 2D array probe capable of generating three-dimensional volume data may be used. In this case, the position information can be converted based on the volume data generated by the ultrasonic probe, in place of the volume data which is acquired from the image server 200 in Step S2. A guide marker may be superimposed on the volume data.

Where the 2D array probe is employed, the transmission/reception beams in the same direction can be obtained by merely using the same coordinates of the ultrasonic probe between first examination of a follow-up and the second and subsequent examinations of the follow-up. To be specific, the coordinates of the ultrasonic probe used for measuring the flow velocity in the first examination of a follow-up and the direction of transmission and reception beams are converted into data based on the volume data coordinate system acquired from the image server, and the resultant data are stored in the memory circuitry. In the second examination of the follow-up, the coordinates of the ultrasonic probe expressed in the volume data coordinate system are converted into coordinates used in the first examination of the follow-up, and the ultrasonic diagnostic apparatus generates volume data based on the coordinates. In the volume data, thus generated, a transmission/reception direction which is the same as that used in the first examination of the follow-up is detected, and beams are transmitted and received in this direction. By virtue of this feature, the reproducibility of the flow velocity measurement can be easily enhanced.

In connection with the present embodiment, reference was made to the case where Doppler spectrum data is generated at the same position in each measurement. However, color Doppler data may be generated at the same position in each measurement. In this case, the ultrasonic probe has to be at the same position between past diagnosis and current diagnosis. In addition, the transmission angle and focusing distance at each focus position required for generating color Doppler data have to be the same as those used in the past measurement of the flow velocity.

In connection with the present embodiment, reference was made to the case where Doppler spectrum data is automatically generated when the current guide marker is moved to the position of the target guide marker 111. However, this is in no way restricting. That is, the operator may operate the input circuitry 11 and designate the generation of Doppler spectrum data after moving the current guide marker 110 to the position of the target guide marker 111.

In connection with the present embodiment, reference was made to the case where the volume image 108, current guide marker 110 and target guide marker 111 are superimposed when they are displayed on the display circuitry 8. However, the volume image 108 does not have to be displayed. In this case as well, the operator moves the ultrasonic probe 4 in such a manner that the current guide marker 110 is displayed on the same position as the target guide marker 111. By so doing, the operator can move the ultrasonic probe 4 to the same position as it was located in the past diagnosis.

In connection with the present embodiment, reference was made to the case where the position information acquired by the position information acquiring circuitry 202 is the position information on the ultrasonic probe 4. However, the position information acquired by the position information acquiring circuitry 202 may be information on the position where a scan is being performed. For example, the central point in the scanning area in the B-mode image 102 may be acquired as position information.

In connection with the present embodiment, reference was made to the case where the ultrasonic diagnostic apparatus 100 does not comprise the position sensor 201, position information acquiring circuitry 202 or magnetic field generating circuitry 203. However, the ultrasonic diagnostic apparatus 100 may be configured to comprise at least one of the position sensor 201, position information acquiring circuitry 202 and magnetic field generating circuitry 203.

In connection with the present embodiment, reference was made to the case where three kinds of data, namely B-mode data, color Doppler data and Doppler spectrum data, are generated in the order mentioned. However, two kinds of data, namely B-mode data and Doppler spectrum data, may be generated in the order mentioned. Doppler spectrum data does not have to be generated using pulse Doppler data; it may be generated using continuous-wave Doppler data. Since no depth information is used in the continuous-wave Doppler method, guide data is generated using the position information and angle information on the ultrasonic probe 4.

In connection with the present embodiment, reference was made to the case where the ultrasonic diagnostic apparatus used in the first examination of a follow-up is the same as the ultrasonic diagnostic apparatus used in the second and subsequent examinations of the follow-up. As long as the position information on the ultrasonic probe of the first examination of the follow-up is used in the second and subsequent examinations, the ultrasonic diagnostic apparatus used for the first examination may be different from that used for the second and subsequent examinations.

In connection with the present embodiment, reference was made to the case where the position information on the ultrasonic probe 4 acquired by the position information acquiring circuitry 202 in the first examination of a follow-up is subjected to conversion in real time. However, if the memory circuitry 7 stores both position information on the ultrasonic probe 4 used in the first examination of a follow-up and volume data acquired from the image server 200, then the position information stored in the memory circuitry 7 may be used in the second and subsequent examinations of the follow-up.

In connection with the above embodiment, the display circuitry 8 displays both probe markers 110-1 and 111-1 and range gate markers 110-2 and 111-2. However, the present embodiment is not limited to this. The display circuitry 8 may be configured to display either the probe markers 110-1 and 111-1 or the gate guide markers 110-2 and 111-2, if the operator can arrange the current ultrasonic probe 4 at the same position and in the same direction as the ultrasonic probe 4 in a past ultrasonic scan.

In the above embodiment, the guide markers were described as markers indicating the position information on a scan position in Doppler measurement. However, the present embodiment is not limited to this. For example, the guide markers may indicate the position information on a scan position in color Doppler measurement. In this case, the position information on the scan position is defined as position information on a ROI in color Doppler measurement. The display circuitry 8 displays both a past ROI guide marker indicating a ROI in a past ultrasonic scan and a current ROI guide marker indicating a ROI in a current ultrasonic scan in such a manner that the positions of the two guide markers are correlated with each other based on the information on the scan position in the past ultrasonic scan and the information on the scan position in the current ultrasonic scan. By virtue of this feature, the ultrasonic probe 4 can be moved to a past scan position easily and accurately in the color Doppler measurement as well.

As can be seen from the above, the present embodiment improves the reproducibility in the measurement of a flow velocity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
   converting circuitry which converts position information of an ultrasonic probe or a scanning line in a first coordinate system into position information in a second coordinate system which is used as a reference coordinate system;
   processing circuitry which controls an angle of a scanning line and a focusing distance of a current Doppler measurement at a time of performing Doppler measurement for generating Doppler spectrum data;
   memory circuitry which stores an angle of a scanning line and a focusing distance in a past Doppler measurement;
   generating circuitry which generates guide data based on first position information obtained in the past Doppler measurement and converted by the converting circuitry, second position information obtained in the current Doppler measurement and converted by the converting circuitry, and the angle of the scanning line and the focusing distance in the past Doppler measurement which are stored by the memory circuitry; and
   display control circuitry which displays an image based on the guide data.

2. The ultrasonic diagnostic apparatus according to claim 1, wherein
   the second coordinate system is a coordinate system to which volume data belong, the volume data is data of a three-dimensional medical image,
   the display control circuitry displays the image based on the guide data, with superimposing the image on the three-dimensional medical image.

3. The ultrasonic diagnostic apparatus according to claim 2, wherein
   the volume data is data obtained from an image server.

4. The ultrasonic diagnostic apparatus according to claim 1, wherein
   the display control circuitry displays, as the image based on the guide data, a target position guide marker which indicates a position and a direction of the ultrasonic probe in the past Doppler measurement, and a current position display marker which indicates a position and a direction of the ultrasonic probe in the current Doppler measurement.

5. The ultrasonic diagnostic apparatus according to claim 4, wherein
the display control circuitry displays, as the image based on the guide data, an arrow-shaped marker that guides the current position guide marker to the target position guide marker so that the current position guide marker and the target position guide marker are superimposed.

6. The ultrasonic diagnostic apparatus according to claim 1, wherein
the generating circuitry calculates a degree of matching between the first position information and the second position information, and
the display control circuit displays the degree of matching.

7. The ultrasonic diagnostic apparatus according to claim 1, wherein
the display control circuitry displays a Doppler spectrum image generated by the past Doppler measurement, and a Doppler spectrum image generated by the current Doppler measurement.

8. The ultrasonic diagnostic apparatus according to claim 1, wherein
the display control circuitry displays a value based on a rate of blood flow measured in the past Doppler measurement, and a value based on a rate of blood flow measured in the current Doppler measurement.

9. The ultrasonic diagnostic apparatus according to claim 1, wherein
the processing circuitry controls the angle of the scanning line and the focusing distance in the current Doppler measurement based on the angle of the scanning line and the focusing distance in the past Doppler measurement which are stored by the memory circuitry.

10. The ultrasonic diagnostic apparatus according to claim 9, wherein
the processing circuitry starts measuring a rate of blood flow when the first position information matches the second position information.

* * * * *